(12) United States Patent
Bleckmann et al.

(10) Patent No.: US 12,171,860 B2
(45) Date of Patent: Dec. 24, 2024

(54) BODY MILK

(71) Applicant: BEIERSDORF AG, Hamburg (DE)

(72) Inventors: Andreas Bleckmann, Ahrensburg (DE); Sabine Sellckau, Hamburg (DE); Svea Wischhoefer, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 18/522,850

(22) Filed: Nov. 29, 2023

(65) Prior Publication Data
US 2024/0285503 A1    Aug. 29, 2024

(30) Foreign Application Priority Data
Feb. 21, 2023  (DE) .......................... 102023201528.5

(51) Int. Cl.
| | | |
|---|---|---|
| *A61K 8/73* | (2006.01) | |
| *A61K 8/37* | (2006.01) | |
| *A61K 8/67* | (2006.01) | |
| *A61K 8/86* | (2006.01) | |
| *A61Q 19/00* | (2006.01) | |

(52) U.S. Cl.
CPC ................... *A61K 8/73* (2013.01); *A61K 8/37* (2013.01); *A61K 8/67* (2013.01); *A61K 8/86* (2013.01); *A61Q 19/00* (2013.01)

(58) Field of Classification Search
None
See application file for complete search history.

(56) References Cited

U.S. PATENT DOCUMENTS

| | | |
|---|---|---|
| 4,605,691 A | 8/1986 | Balazs et al. |
| 4,713,448 A | 12/1987 | Balazs et al. |
| 2006/0161121 A1* | 7/2006 | Klaveness ................ A61K 8/22  604/289 |
| 2007/0003511 A1 | 1/2007 | Schulz et al. |
| 2015/0366784 A1 | 12/2015 | Ramirez et al. |
| 2021/0169771 A1 | 6/2021 | Schecker et al. |
| 2024/0148637 A1 | 5/2024 | Timm et al. |

FOREIGN PATENT DOCUMENTS

| | | | | |
|---|---|---|---|---|
| CN | 109303735 A | * | 2/2019 | ............ A61K 8/41 |
| DE | 10148313 A1 | | 4/2003 | |
| DE | 10204526 A1 | | 8/2003 | |
| DE | 10361568 A1 | | 7/2005 | |
| DE | 20221822 U1 | | 2/2008 | |
| DE | 102017221672 A1 | | 6/2019 | |
| DE | 102018217130 A1 | | 4/2020 | |
| EP | 2926801 A1 | * | 10/2015 | ............ A61K 8/064 |
| WO | 2022157061 A1 | | 7/2022 | |

OTHER PUBLICATIONS

Database GNPD Mintel, anonymous: "BB Cream SPF 50+" Database accession No. 8912723, Aug. 5, 2021.

* cited by examiner

*Primary Examiner* — Dale R Miller
(74) *Attorney, Agent, or Firm* — Abel Schillinger, LLP

(57) ABSTRACT

A body milk for improved skin moisture level comprises hyaluronic acid and/or salts thereof. PEG-40 Sorbitan Perisostearate and Polyglyceryl-3 Diisostearate and Tocopherol, and one or more lipids selected from isopropyl palmitate, isododecane, almond oil, the preparation being free of BHT.

20 Claims, No Drawings

BODY MILK

CROSS-REFERENCE TO RELATED APPLICATIONS

The present application claims priority under 35 U.S.C. § 119 of German Patent Application No. 102023201528.5, filed Feb. 21, 2023, the entire disclosure of which is expressly incorporated by reference herein.

BACKGROUND OF THE INVENTION

1. Field of the Invention

The present invention relates to a cosmetic or dermatological preparation comprising hyaluronic acid and/or salts thereof, Polyglyceryl-3 Diisostearate, PEG-40 Sorbitan Perisostearate and Tocopherol, and one or more lipids selected from isopropyl palmitate, isododecane and almond oil (*Prunus Amygdalus Dulcis* Oil).

2. Discussion of Background Information

External influences, in particular environmental influences, sun exposure and skin cleansing, lead to the skin's moisture balance being disturbed.

In order for the skin to be able to perform the full range of its biological functions, it requires regular cleansing and care. Skin care products, generally creams, ointments or lotions, mostly serve for moisturizing and refatting the skin. Active ingredients are commonly added thereto, which are intended to regenerate the skin and for example to prevent and reduce the premature aging thereof (e.g. the appearance of fine lines and wrinkles).

To care for the skin, consumers are nowadays offered a plurality of cosmetic preparations, usually in the form of creams and lotions, i.e., as an emulsion. Products which temporarily or permanently delay or eliminate the aging phenomena of the skin, negative environmental influences and even skin diseases are of ever-increasing importance. In addition to water for skin moisturization and oils and lipids for refatting of the skin, such skin care products comprise a plurality of active ingredients, auxiliaries and additives.

Hyaluronic acid (also according to nomenclature hyaluronan, abbreviation HA, CAS: 9004-61-9) is a glycosaminoglycan that represents an important constituent of connective tissue. HA is characterized by a repeating disaccharide unit according to the following structure:

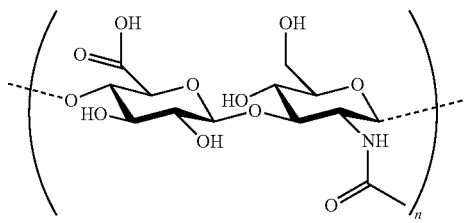

HA is a linear, acidic polysaccharide which consists of a plurality of alternating disaccharide units of 1,3-glycosidically linked N-acetyl-ß-D-glucosamine (GlcNAc) and ß-D-glucuronic acid (GlcA) molecules. Each of the disaccharidic base units is linked to the next by a ß(1-4) bond. The number of base units can reach more than 10 000 with a molar mass of 4 million daltons. Due to their hydrophilic acid groups and the hydroxyl groups, HA has the ability to form a plurality of hydrogen bonds via which hydrations can be added and it is therefore homogeneously miscible with water. In aqueous solution, HA is capable of binding more and more water with extension of the average chain spacing, since the negative charges cause repulsion of the chain sections that are close to one another. Under physiological conditions, the carboxyl groups of HA are practically completely dissociated and represent a polyanionic compound. The term hyaluronic acid is generally used irrespective of whether HA itself or the salts are meant. Due to the viscoelastic properties and its biocompatibility, HA is of therapeutic importance as an injection solution in ophthalmology, orthopedics and cosmetic surgery.

Hyaluronic acid is a natural constituent of the skin. In cosmetic products, use is made of two forms of hyaluronic acid, a short-chain and a long-chain form. The short-chain hyaluronic acid penetrates the upper layer of the skin and influences the inner moisture balance. By contrast, the long-chain hyaluronic acid is intended to exhibit a plumping-up effect on the skin. It effectively binds moisture in the upper layer of the skin. Its moisture-binding effect arises from the fact that it releases its hydrate mantle only gradually and thus acts on the skin over a long period. HA has the further functions of supplying connective tissue and skin with moisture and nutrients.

The sodium salt of hyaluronic acid is also used, among other things, as a moisturizer (humectant) for the production of cosmetic products (Römpp online Lexicon Version 2.5, 2004).

Hyaluronic acid is commercially available in the cross-linked state (for example Hylaform®, a crosslinked hyaluronic acid from Biomatrix, NJ, USA; for preparation cf. also U.S. Pat. Nos. 4,713,448, 4,605,691, APC® from Fidia, Incert® from Anika Therapeutics, Intergel® from LifeCore or Restylane® from Q-Med).

Recently, there has been a growing trend toward "natural" cosmetics, the ingredients of which should as far as possible no longer come from petroleum products or be chemically synthesized. This trend overlaps nowadays with the trend toward "vegan" products. The search for alternative ingredients that meet these criteria poses particular challenges for product developers. This is because the replacement of known ingredients such as mineral oils, silicone oils and polyacrylates is practically always at the expense of disadvantages with respect to the product properties. The preparations become unstable and sensorially unattractive, which is unpleasantly noticeable for example when spreading the preparation on the skin and by the inadequate absorption capacity. These problems occur in particular with water-in-oil emulsions (W/O emulsions), which have recently enjoyed a resurgence in popularity. For instance, W/O emulsions without mineral oils and mineral waxes and without polyethylene glycol ethers or esters (so-called PEG derivatives) tend to be more unstable. In the case of relatively long storage periods, particularly at relatively high temperatures, phase separations in the form of oil and/or water separations rapidly occur that also cannot readily be compensated for by a relatively high emulsifier content.

In view of the foregoing, it would be advantageous to have available a cosmetic or dermatological preparation which as far as possible dispenses with BHT, polyethylene glycol ethers and esters and advantageously is free of mineral oil, paraffin wax, microcrystalline wax, shellac wax and polyethylene waxes, free of polyacrylates, crosslinked acrylate/C10-C30 alkyl acrylate polymers and vinylpyrrolidone/hexadecene copolymers, and free of 3-(4-methylbenzylidene)camphor, 2-hydroxy-4-methoxybenzophenone (INCI: Oxybenzone), 2-ethylhexyl 4-methoxycinnamate (INCI: Octyl Methoxycinnamate), ethylhexyl 2-cyano-3,3-diphenylacrylate (INCI: Octocrylene), parabens (particularly methyl, propyl and butyl paraben), methylisothiazolinone, chloromethylisothiazolinone and DMDM hydantoin.

SUMMARY OF THE INVENTION

The present invention provides a cosmetic or dermatological preparation which comprises hyaluronic acid and/or salts thereof, Polyglyceryl-3 Diisostearate, PEG-40 Sorbitan Perisostearate and Tocopherol, and one or more lipids selected from isopropyl palmitate, isododecane and almond oil (*Prunus Amygdalus Dulcis* Oil).

The preparation according to the invention is advantageously provided as a water-in-oil (W/O) emulsion and is a skin-moisturizing body milk.

Ideally, preparations according to the invention are also free of BHT, mineral oil, paraffin wax, microcrystalline wax, shellac wax and polyethylene waxes, free of polyacrylates, crosslinked acrylate/C10-C30 alkyl acrylate polymers and vinylpyrrolidone/hexadecene copolymers, and free of 3-(4-methylbenzylidene)camphor, 2-hydroxy-4-methoxybenzophenone (INCI: Oxybenzone), 2-ethylhexyl 4-methoxycinnamate (INCI: Octyl Methoxycinnamate), ethylhexyl 2-cyano-3,3-diphenylacrylate (INCI: Octocrylene), parabens (particularly methyl, propyl and butyl paraben), methylisothiazolinone, chloromethylisothiazolinone and DMDM hydantoin, polyethylene glycol ethers and polyethylene glycol esters, except for the substances present according to the invention, such as PEG-40 Sorbitan Perisostearate.

"Free of" means that the proportion thereof is less than 0.1% by weight, e.g., less than 0.05% by weight, or less than 0.01% by weight, should one or another substance still be present due to entrainments or contaminations.

Although DE 102017221672 and DE 102018217130, the entire disclosures of which are incorporated by reference herein, are known to those skilled in the art, these documents were unable to point the way to the present invention.

Hyaluronic acid and/or salts thereof are preferably added at a proportion of from 0.0005% to 5% by weight, preferably of from 0.001% to 1% by weight, based on the total weight of the preparation.

The preparation advantageously comprises Polyglyceryl-3 Diisostearate at a proportion of from 0.1% to 3.0% by weight; particularly preferred at a proportion of from 0.5% to 2% by weight, based on the total weight of the preparation.

The preparation advantageously comprises PEG-40 Sorbitan Perisostearate at a proportion of from 0.1% to 3.0% by weight; particularly preferred at a proportion of from 0.5% to 2% by weight, based on the total weight of the preparation.

Advantageously, PEG-40 Sorbitan Perisostearate and Polyglyceryl-3 Diisostearate are present in a weight ratio of from 3:1 to 1:2, in particular in a ratio of from 2:1 to 1:1.

Tocopherol is advantageously present at a proportion of from 0.01% to 2.0% by weight; particularly preferred at a proportion of from 0.05% to 1.5% by weight, based on the total weight of the preparation.

It is advantageous if one or more, preferably all lipids selected from isopropyl palmitate, isododecane, almond oil (*Prunus Amygdalus Dulcis* Oil) are in each case present at a proportion of from 0.1% to 15% by weight, based on the total weight of the preparation.

If the preparation comprises isopropyl palmitate, this component is advantageously used according to the invention at a proportion of from 1.0% to 15.0% by weight, based on the total weight of the preparation. Particular preference is given to a proportion of from 2% to 12% by weight.

Advantageous embodiments of the present invention are further characterized in that the preparation comprises one or more vegetable oils.

It is preferred according to the invention if the preparation comprises almond oil (INCI: *Prunus Amygdalus Dulcis* Oil).

If the preparation comprises almond oil (INCI: *Prunus Amygdalus Dulcis* Oil), this component is advantageously used according to the invention at a concentration of from 0.1% to 0.5% by weight, based on the total weight of the preparation.

Advantageously, the preparation according to the invention comprises one or more further skin humectants, particularly glycerin. These are each present preferably at a proportion of from 2% to 15% by weight, in particular of from 3% to 10% by weight, advantageously of from 4% to 8% by weight, in each case based on the total weight of the preparation.

Humectants, also referred to as moisturizers, are substances or substance mixtures which give cosmetic or dermatological preparations the property, once applied to or spread on the surface of the skin, of reducing the loss of moisture from the horny layer (also known as transepidermal water loss (TEWL)) and/or of having a beneficial effect on the hydration of the horny layer.

Advantageous moisturizers in the sense of the present invention are for example glycerin, butylene glycol, propylene carbonate. Further humectants are for example polymeric moisturizers from the group of the water-soluble and/or water-swellable polysaccharides and/or those that can be gelled with the aid of water.

Surprisingly, the combination of one or more lipids according to the invention, Polyglyceryl-3 Diisostearate, PEG-40 Sorbitan Perisostearate and hyaluronic acid or salt thereof, and optionally glycerin, was found to be a skin moisture-promoting complex, called a moisture complex according to the invention.

The capacitance measurement principle of the Corneometer® is used worldwide and serves to determine the skin moisture level. Corneometer values can therefore be used to assess the skin's moisture balance and determined Corneometer data give an indication of the moisture content of the skin.

The combination according to the invention, the skin moisture-promoting complex, exhibits in each case higher and therefore improved Corneometer values in comparison with the untreated area of skin and in comparison with the area of skin treated only with in each case one constituent of the complex.

The moisture complex according to the invention promotes skin moisture and has a beneficial effect on the hydration of the horny layer of the skin.

In addition, the preparation according to the invention may comprise further ingredients that are customary for cosmetics.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those of skill in the art how the several forms of the present invention may be embodied in practice.

Example

The examples which follow are intended to illustrate the present invention without limiting it. Unless otherwise indicated, all amounts, proportions and percentages are based on the weight and the total amount or on the total weight of the preparations.

| INCI | % by weight | % by weight | % by weight |
|---|---|---|---|
| Tocopherol | 0.05 | 0.5 | 0.6 |
| Sodium Hyaluronate | 0.001 | 0.0015 | 0.002 |
| Cera Microcristallina + Paraffinum Liquidum + Tocopheryl Acetate + BHT | 3 | 2.5 | 4 |
| Paraffinum Liquidum | 9 | 9.5 | 8 |
| Isopropyl Palmitate | 3 | 3.5 | 2.5 |
| Isododecane | 4.5 | 4 | 5 |
| Prunus Amygdalus Dulcis Oil | 0.2 | 0.3 | 0.1 |
| PEG-40 Sorbitan Perisostearate | 1.77 | 1.9 | 2 |
| Polyglyceryl-3 Diisostearate + Aqua | 1.43 | 1.5 | 1.6 |
| Perfume | 0.35 | 0.3 | 0.4 |
| Glycerin + Aqua | 5.3 | 6 | 7 |
| Citric Acid | 0.086 | 0.09 | 0.08 |
| Sodium Citrate + Aqua | 0.174 | 0.18 | 0.17 |
| Potassium Sorbate | 0.125 | 0.13 | 0.1 |
| Magnesium Sulfate | 0.7 | 0.8 | 0.6 |
| Aqua | To 100 | To 100 | To 100 |

The invention claimed is:

1. A cosmetic or dermatological preparation, wherein the preparation is free of mineral oil, paraffin wax and microcrystalline wax and comprises hyaluronic acid and/or salts thereof, Polyglyceryl-3 Diisostearate, PEG-40 Sorbitan Perisostearate, Tocopherol, and one or more lipids selected from isopropyl palmitate, isododecane and almond oil (*Prunus Amygdalus Dulcis* Oil).

2. The preparation of claim 1, wherein the preparation is a water-in-oil emulsion (W/O emulsion).

3. The preparation of claim 1, wherein the preparation further is free of BHT, shellac wax and polyethylene waxes, free of polyacrylates, crosslinked acrylate/C10-C30 alkyl acrylate polymers and vinylpyrrolidone/hexadecene copolymers, and free of 3-(4-methylbenzylidene) camphor, 2-hydroxy-4-methoxybenzophenone, 2-ethylhexyl 4-methoxycinnamate, ethylhexyl 2-cyano-3,3-diphenylacrylate, parabens, methylisothiazolinone, chloromethylisothiazolinone, DMDM hydantoin, polyethylene glycol ethers and polyethylene glycol esters, except for PEG-40 Sorbitan Perisostearate.

4. The preparation of claim 1, wherein the preparation comprises hyaluronic acid and/or salts thereof in a concentration of from 0.0005% to 5% by weight, based on a total weight of the preparation.

5. The preparation of claim 4, wherein the preparation comprises hyaluronic acid and/or salts thereof in a concentration of from 0.001% to 1% by weight.

6. The preparation of claim 1, wherein the preparation comprises Polyglyceryl-3 Diisostearate in a concentration of from 0.1% to 3.0% by weight, based on a total weight of the preparation.

7. The preparation of claim 6, wherein the preparation comprises Polyglyceryl-3 Diisostearate in a concentration of from 0.5% to 2% by weight.

8. The preparation of claim 1, wherein the preparation comprises PEG-40 Sorbitan Perisostearate in a concentration of from 0.1% to 3.0% by weight, based on a total weight of the preparation.

9. The preparation of claim 8, wherein the preparation comprises PEG-40 Sorbitan Perisostearate in a concentration of from 0.5% to 2% by weight.

10. The preparation of claim 1, wherein the preparation comprises PEG-40 Sorbitan Perisostearate and Polyglyceryl-3 Diisostearate in a weight ratio of from 3:1 to 1:2.

11. The preparation of claim 1, wherein the preparation comprises PEG-40 Sorbitan Perisostearate and Polyglyceryl-3 Diisostearate in a weight ratio of from 2:1 to 1:1.

12. The preparation of claim 1, wherein the preparation comprises Tocopherol in a concentration of from 0.01% to 2.0% by weight, based on a total weight of the preparation.

13. The preparation of claim 1, wherein the preparation comprises one or more of isopropyl palmitate, isododecane, almond oil (*Prunus Amygdalus Dulcis* Oil) in a concentration of in each case from 0.1% to 15% by weight, based on a total weight of the preparation.

14. The preparation of claim 1, wherein the preparation comprises one or more further skin humectants.

15. The preparation of claim 1, wherein the preparation further comprises glycerin.

16. The preparation of claim 14, wherein the one or more further skin humectants are present in a concentration of from 2% to 15% by weight, based on a total weight of the preparation.

17. A cosmetic or dermatological preparation, wherein the preparation is free of mineral oil, paraffin wax and microcrystalline wax and comprises hyaluronic acid and/or salts thereof, Polyglyceryl-3 Diisostearate, PEG-40 Sorbitan Perisostearate, Tocopherol, with isopropyl palmitate, isododecane and optionally almond oil (*Prunus Amygdalus Dulcis* Oil) being the only lipids present in the preparation.

18. The preparation of claim 17, wherein the preparation comprises almond oil.

19. The preparation of claim 17, wherein the preparation is a water-in-oil emulsion (W/O emulsion).

20. The preparation of claim 17, wherein the preparation comprises one or more of isopropyl palmitate, isododecane, almond oil (*Prunus Amygdalus Dulcis* Oil) in a concentration of in each case from 0.1% to 15% by weight, based on a total weight of the preparation.

* * * * *